United States Patent [19]

Kobayashi et al.

[11] Patent Number: 4,931,389
[45] Date of Patent: Jun. 5, 1990

[54] METHOD FOR THE PREPARATION OF MULTIPLE GLUCOSYL BRANCHED-CYCLODEXTRINS

[75] Inventors: Shoichi Kobayashi, Tsuchiura; Katsuhiko Mikuni, Yokohama; Mitsuru Monma; Toshiya Takano, both of Tsukuba; Kozo Hara, Yokohama; Hitoshi Hashimoto, Kamakura, all of Japan

[73] Assignees: Director of National Food Research Institute, Minstry of Agriculture, Forestry and Fisheries, Ibaraki; Ensuiko Sugar Regining Co., Ltd., Kanagawa, both of Japan

[21] Appl. No.: 236,591

[22] Filed: Aug. 25, 1988

[30] Foreign Application Priority Data

May 13, 1988 [JP] Japan .................. 63-114778

[51] Int. Cl.$^5$ .............. C12P 19.22; C12P 19/18; C07G 3/00; C08B 37/16
[52] U.S. Cl. ........................... 435/95; 435/96; 435/97; 435/98; 536/4.1; 536/103; 536/123
[58] Field of Search ............... 435/95, 98, 205, 210, 435/233; 536/1.1, 4.1, 123, 103, 124

[56] References Cited

U.S. PATENT DOCUMENTS 4,668,626 5/1987 Kobayashi et al. .............. 435/95

OTHER PUBLICATIONS

Handbook of Amylases and Related Enzymes, p. 125, (1988).
Chemical Abstracts, 107(18):156851s, (1987).

Primary Examiner—Ronald W. Griffin
Assistant Examiner—Pamela S. Webber
Attorney, Agent, or Firm—Frishauf, Holtz, Goodman & Woodward

[57] ABSTRACT

In a method for preparing multiple glucosyl branched-cyclodextrins, a debranching enzyme is contacted to a mixture of maltose or a substance containing maltooligosaccharide such as maltose with a cyclodextrin to obtain a reaction product from which a branched-cyclodextrin is then separated; said branched-cyclodextrin is converted to glycosyl-cyclodextrin under the action of glucoamylase, which is thereafter mixed with maltose or a substance containing maltooligosaccharide such as maltose; and the resulting mixture is successively acted on by a debranching enzyme and glucoamylase.

3 Claims, 1 Drawing Sheet

METHOD FOR THE PREPARATION OF MULTIPLE GLUCOSYL BRANCHED-CYCLODEXTRINS

BACKGROUND OF THE INVENTION

The present invention relates to a method for the preparation of multiple glucosyl, branched-cyclodextrins.

Preparation of branched cyclodextrins, and utilization and development thereof have been in rapid progress due to their excellent physical properties such as high solubility. To date, there have been known methods for preparing single branched-cyclodextrins having one branched-dextrin such as $\alpha$-1,4 glucane and panose attached to their cyclodextrin rings, and multiple branched-cyclodextrins having two branches of malto-oligosaccharides, such as glucose, maltose and maltotriose, attached to their cyclodextrin rings, for instance, diglucosyl-cyclodextrin having two glucoses attached to the same cyclodextrin ring, dimaltosyl-cyclodextrin having two maltoses attached to the same cyclodextrin ring and glucosyl- or maltosylcyclodextrin having glucose or maltose branches attached to the same cyclodextrin ring.

These cyclodextrins are prepared by allowing a cyclodextrin-synthesizing enzyme to act upon branched-dextrins or permitting a mixture of an $\alpha$-1,4 glucan such as maltose or maltotriose or a branched-dextrin such as panose with a cyclodextrin to act upon a debranching enzyme. There is also a method for preparing branched-cyclodextrins by allowing a mixture of malto-oligosyl fluoride or glucosyl fluoride with a cyclodextrin to act upon a debranching enzyme.

Single-branched cyclodextrins having one branch are much higher in solubility than the original cyclodextrins, and can be used in wider applications. However, since such single-branched cyclodextrins having one branch, e.g., single-branched $\beta$-cyclodextrin are affected by amylases of *Aspergillus oryzae* (Taka-amylase), there has been an increasing demand for cyclodextrins highly resistant to such enzymes and their efficient preparation.

In particular, there is now a strong demand for multiple glucosyl branched-cyclodextrins, since they are hardly affected by amylases and excel in solubility. However, the preparation of multiple glucosyl branched-cyclodextrins so far considered merely involves the conversion of branch portions of conventionally produced multiple maltosyl branched-cyclodextrins to glucosyl groups by cutting with glucoamylase. In addition, the yields of multiple maltosyl cyclodextrins in conventional methods are low and barely 22.3% at most. Thus, not until now has any efficient method for preparing multiple glucosyl branched-cyclodextrins been developed.

Heretofore, there have been known methods for producing from maltose, maltotriose, panose and cyclodextrins maltosylcy-cyclodextrins, maltotriosylcyclodextrins, panosyl-cyclodextrins and dimaltosylcyclodextrins with the use of reverse synthesis reactions of debranching enzymes such as pullulanase and, on the basis of such findings, the preparation of single and multiple branched-cyclodextrins has been established. Further, it has been known that multiple branched-cyclodextrins such as glucosyl-cyclodextrin maltosylcyclodextrin are formed from malto-oligosaccharides and glucosyl-cyclodextrins by reverse synthesis reactions of debranching enzymes. Still further, it has been known that branch portions bonded to such cyclodextrins can be cut into glucosyl groups under the action of glucoamylase.

SUMMARY OF THE INVENTION

An object of the present invention is therefore to establish a method for preparing multiple glucosyl branched-cyclodextrins through a combination of such findings as mentioned above.

In order to achieve this object, maltose was first mixed with a cyclodextrin according to conventional methods to obtain maltosyl-cyclodextrin by the reverse synthesis reaction of a debranching enzyme. After separating the reaction mixture into maltose and cyclodextrin components (branched and unbranched cyclodextrins), the cyclodextrin components are then acted on by glucoamylase to form a glucosyl-cyclodextrin not acted on by the debranching enzyme and an unreacted cyclodextrin. After separating and removing the produced glucose, the cyclodextrin components are again mixed with maltose and acted on by the debranching enzyme and glucoamylase. As a result, it was found that 70% or more of the initial cyclodextrin was converted to a branched-cyclodextrin by the three reactions, and the conversion to the multiple glucosyl branched-cyclodextrin reached as high as 35% or more. Thus, the present invention has been accomplished on the basis of such findings.

BRIEF DESCRIPTION OF THE DRAWINGS

The above and other objects and features of the present invention will now become apparent from a reading of the following detailed description with reference to FIGURE attached hereto, which is a flow sheet illustrating one embodiment of the process according to the present invention.

DETAILED DESCRIPTION OF THE INVENTION

Figure 1:
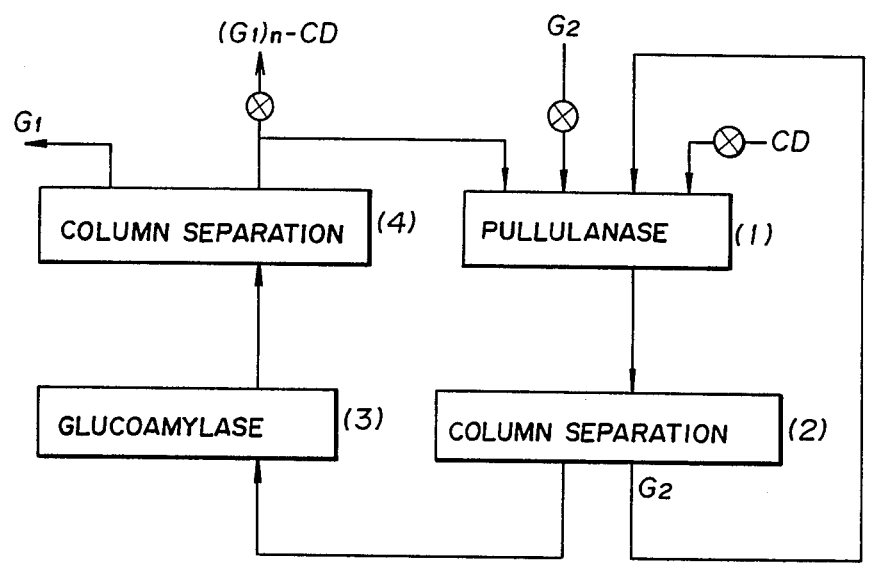

In the present disclosure, it is understood that the term "branched-cyclodextrins" refers generally to cyclodextrins having branch such as glucose and maltose attached to their cyclodextrin ring, and the term "multiple branched-cyclodextrins" to cyclodextrins having two or more branches attached to their cyclodextrin ring. If a cyclodextrin has one type of branches the number of which is somewhere in between 2 and a larger figure, then it shall be called, for instance, the multiple glucosyl branched-cyclodextrin in which the type of branches is interposed between the terms "multiple" and "cyclodextrin". Especially in the case of cyclodextrins having branches limited in terms of type and number, they shall hereinafter be referred to as diglucosyl-cyclodextrin, glucosyl and maltosyl-cyclodextrin by way of example. In the schematical formulae to be given later, cyclodextrin, glucosyl-cyclodextrin, maltosyl-cyclodextrin, glucose, maltose and so on will be abbreviated as CD, $G_1$-CD, $G_2$-CD, $G_1$, $G_2$ and so on, respectively.

The present method is characterized by producing the end multiple glucosyl branched-cyclodextrins through a combination of the reverse synthesis reaction of the debranching enzyme with the hydrolysis reaction of glucoamylase.

In more detailed terms, the present invention provides a method for preparing multiple glucosyl branched-cyclodextrins characterized in that a cyclodextrin is mixed with a branching saccharide or saccharides selected from malto-oligosaccharides to form a branch-cyclodextrin by the reverse synthesis reaction of a debranching enzyme; after the separation of the saccharide(s) for branching, the branched-cyclodextrin of the cyclodextrin components is converted to glucosyl-cyclodextrin under the action of glucoamylase; and an unreacted cyclodextrin and glucosylcyclodextrin are again mixed with the saccharide(s) for branching and converted to a multiple branched-cyclodextrin under the action of the debranching enzyme, and in that such a series of reactions is repeated thereby to increase the branched-cyclodextrin content.

The more the number of repetition of the reverse synthesis reaction of the debranching enzyme-the action of glucoamylase, the higher the content of the multiple glucosyl branched-cyclodextrin and, eventually, the cyclodextrin is all converted to the multiple glucosyl branched-cyclodextrin.

FIG. 1 illustrates one embodiment of the process of the present invention, which may possibly be used in wider applications.

Referring now to step (1) of FIG. 1, any debranching enzyme such as commercially available pullulanase may be used as the enzymatic material. A membrane reactor making use of free type enzymes may be used in the present invention; however, immobilized enzymes may more advantageously be used for continuous process.

Referring to step (2) of FIG. 1, any material capable of separating the cyclodextrin components and saccharide(s) for branching, such as ODS, ion exchange resins and activated carbon, may be used for column separation. However, since the column separation makes use of an eluent which gives rise to a lowering of substrate concentrations, better results are obtained when concentrators such as reverse osmosis membranes and multiple-effective evaporators are provided on suitable portions on the line. When an ODS column is employed, it is more preferable to carry out ethanol elution for the separation of the cyclodextrin components so as to maintain the performance of the column. However, use may be made of a loose reverse osmosis membrane to simultaneously discharge ethanol and water from within the system.

Referring to step (3) of FIG. 1, either one of free type and immobilized enzymatic materials may be used as the enzyme; however, it is more advantageous to use the immobilized enzymes in continuous systems. Referring to the types of such enzymatic materials to be used, commercially available crude to refined products may be used.

The sugar components leaving step (3) include an unreacted cyclodextrin, glucosyl-cyclodextrin, and glucose which may or may not be removed. Therefore, step (4) may be omitted, whenever possible.

When glucose is not removed, glucose is so accumulated that there is a lowering of reactivity, if the system is of the continuous type. For that reason, once the glucose content reaches a predetermined level, the glucose may be separated from the product on the line for re-use of maltose [(2)-(1)]by using such a moving bed type separation system as used for the separation of GF. Further, this system may also be applicable to the separation of the cyclodextrin and non-cyclodextrin components (oligosaccharides such as glucose and maltose).

As the saccharides for branching, use may be made of maltose, maltose syrup and a mixture of maltose with maltotriose such as "oligotose" as well as syrup or powder syrup containing maltooligosaccharide. The cyclodextrins to be used as the starting material may be $\alpha$-, $\beta$- or $\gamma$-cyclodextrin or a mixture thereof as well as cyclodextrin powder syrup.

When maltose is used as the saccharide for branching, the sugar component varies in the respective steps as summarized below. (1) $G_2 + CD \rightarrow G_2 + CD + G_2 - CD$, (2) $G_2 + CD + G_2 - CD \rightarrow G_2$ (returned to step (1) after concentrated to a predetermined concentration) and $\rightarrow CD + G_2 - CD$, (3) $CD + G_2 - CD \rightarrow G_1 + CD + G_1 - CD$, (4) $G_1 + CD + G_1 - CD \rightarrow G_1$ and $\rightarrow CD + G_1 - CD$ (again returned to step (1) after concentrated to a predetermined concentration).

Through this cycle, the sugar component changes as a whole, as expressed by $CD \rightarrow \rightarrow G_1 - CD \rightarrow \rightarrow (G_1)_n - CD$ (n=2 and 3). When $G_1 + CD + G_1 - CD$ is returned to step (1) in the absence of step (4) and after concentrated to a predetermined concentration, the sugar component also eventually becomes $G_1 + (G_1)_n - CD$ (n=1, 2 and 3). For that reason, products may be obtained while containing glucose, or glucose may be removed at the final stage.

It is possible to prepare products having varied contents of $(G_1)_n - CD$ (n=1, 2 and 3) by selecting the number of this cycle.

According to the present invention, the multiple glucosyl branched-cyclodextrins can be easily mass-produced through a combination of the reverse synthesis reaction of the debranching enzyme with the hydrolysis reaction of glycoamylase, and so their products can be provided at low costs. Further, due to their excellent physical properties such as solubility, the products are expected to be used in wide applications inclusive of food, medical and cosmetic industries. Still further, the products prepared by the present invention are much higher in the content of the branched cyclodextrin than conventional products containing maltosyl-cyclodextrin. In particular, the multiple glucosyl branched-cyclodextrins are advantageous due to their stability so excellent that they are hardly affected by amylases. It is noted that the cyclodextrins having a various number of glucose branches, which are contained in the product of the present invention may be individually isolated for use.

The present invention will be explained specifically but not exclusively with reference to the following examples.

EXAMPLE 1

A sugar liquid containing $\alpha$-cyclodextrin and maltose at a weight ratio of 1:5 and regulated to a substrate concentration of 60% and pH 5.0 was circulated through an immobilized enzyme column at 65° C. for six hours, in which partially refined pullulanase (manufactured by NOVO) was immobilized on a ceramic carrier by the silane coupling method, and was then introduced into an ODS column maintained at room temperature for the separation of maltose. The temperature was then increased to 70° C. for the elution of cyclodextrin components. The eluate was passed through a column of commercially available immobilized glucoamylase and, thereafter, it was again passed through the ODS column in a similar manner as above to remove glucose, thereby obtaining a sugar liquid containing 52.0% of $\alpha$-cyclodextrin, 40.6% of glucosyl-$\alpha$-cylodextrin and 7.4% of diglucosyl-$\alpha$-cyclodextrin.

This sugar liquid was concentrated through a reverse osmosis membrane, and maltose was added to the concentrate in a weight ratio of 5:1, which was in turn regulated to a substrate concentration of 60%. Then, the product was again subjected to the pullulanase, column, glucoamylase and column treatments, thereby obtaining a second sugar liquid containing 33.2% of α-cyclodextrin, 44.0% of glucosyl-α-cyclodextrin and 22.8% of diglucosyl-α-cyclodextrin.

In a similar manner as above, a third sugar liquid was obtained, which contained 25.5% of α-cyclodextrin, 37.2% of glucosyl-α-cyclodextrin and 37.3% of diglucosyl-α-cyclodextrin.

It is noted that sugar analysis was conducted by high performance liquid chromatography under the following conditions: Column —$NH_2$, 5 μ; eluent—50 % acetonitrile; and Flow Rate—0.8 ml.

EXAMPLE 2

Operations were carried out in a similar manner as stated in Example 1, except that α-cyclodextrin was changed to β-cyclodextrin, thereby obtaining a first sugar liquid containing 66.7% of β-cyclodextrin, 26.0% of glucosyl-β-cyclodextrin, 7.0% of diglucosyl-β-cyclodextrin and 0.3% of triglucosyl-β-cyclodextrin; a second sugar liquid containing 44.5% of β-cyclodextrin, 34.7% of glucosyl-β-cyclodextrin, 16.7% of diglucosyl-β-cyclodextrin and 4.1% of triglucosyl-β-cyclodextrin; and a third sugar liquid containing 29.7% of β-cyclodextrin, 34.9% of glucosyl-β-cyclodextrin, 24.5% of diglucosyl-β-cyclodextrin and 10.9% of triglucosyl-β-cyclodextrin.

EXAMPLE 3

Operations were carried out in a similar manner as stated in Example 1, except that α-cyclodextrin was changed to γ-cyclodextrin, thereby obtaining a first sugar liquid containing 63.8% of γ-cyclodextrin, 28.0% of glucosyl-γ-cyclodextrin, 8.0% of diglucosyl-γ-cyclodextrin and 0.2% of triglucosyl-γ-cyclodextrin; a second sugar liquid containing 40.7% of γ-cyclodextrin, 35.9% of glucosyl-γ-cyclodextrin, 18.7% of diglucosyl-γ-cyclodextrin and 4.7% of triglucosyl-γ-cyclodextrin; and a third sugar liquid containing 25.9% of γ-cyclodextrin, 36.9% of glucosyl-γ-cyclodextrin, 26.9% of diglucosyl-γ-cyclodextrin and 10.3% of triglucosyl-γ-cyclodextrin.

What is claimed is:

1. A process for preparing multiple glucosyl branched-cyclodextrins comprising:
    contacting a debranching enzyme with a mixture of maltose or maltooligosaccharide which contains maltose and a cyclodextrin to form a branched cyclodextrin;
    converting said branched cyclodextrin to glucosyl-cyclodextrin by reaction with glucoamylase;
    mixing said glucosyl-cyclodextrin with maltose or maltooligosaccharide which contains maltose;
    contacting the resulting mixture with a debranching enzyme and glucoamylase successively to form a multiple glucosyl branched-cyclodextrin.

2. The process of claim 1 wherein said branched cyclodextrin is maltosyl-cyclodextrin.

3. The process of claim 1 wherein the debranching enzyme is pullulanase.

* * * * *